Nov. 1, 1949. C. O. GRISSINGER Plant Pat. 888
PEACH TREE
Filed Sept. 27, 1948
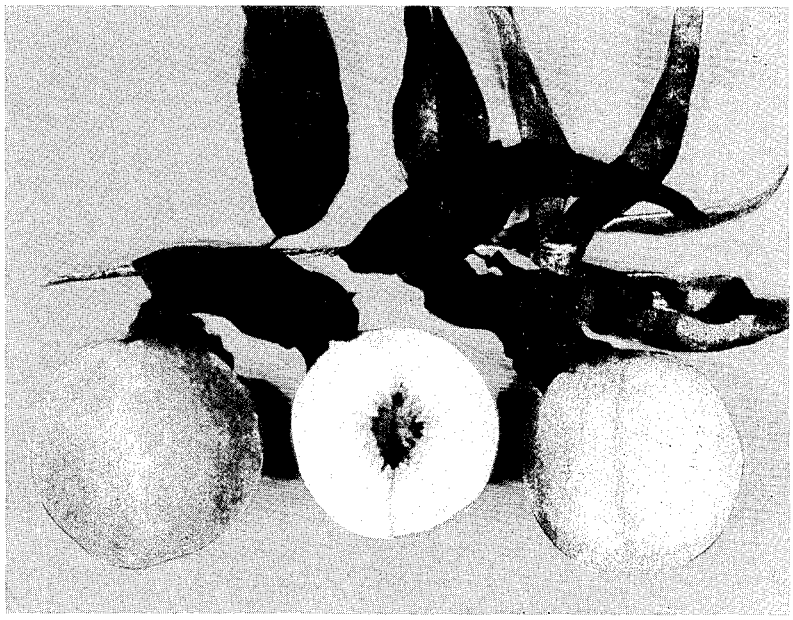
Inventor
C O Grissinger
By Robb & Robb
Attorneys Patented Nov. 1, 1949

Plant Pat. 888

UNITED STATES PATENT OFFICE

888

PEACH TREE

Charles O. Grissinger, New Cumberland, Pa., assignor to Stark Bro's Nurseries and Orchards Company, Louisiana, Mo., a corporation of Missouri Application September 27, 1948, Serial No. 51,391

1 Claim. (Cl. 47—62)

The present discovery relates to a new and distinct variety of peach tree, originating as a bud sport of the well known yellow "J. H. Hale" peach variety.

This new variety is dominantly distinguished from its yellow flesh parent variety in that it bears white fleshed fruit, ripening at the same season as said parent variety, with flavor and quality somewhat superior thereto and slightly less acid, when grown under comparable conditions. The flesh is firm like that of its parent and for this reason this new peach has a better shipping characteristic than most other known white fleshed peaches. Furthermore, the foliage is distinctly the color of "white peach" foliage, since it has no yellowish tint such as is characteristic of yellow varieties. Twigs and limbs are stocky and fruit buds are formed abundantly.

Perhaps one of the most important distinguishing characters of the fruit of this new variety is the distinctive marking thereof with a thin yellow flesh segment along the suture line, extending from the stem to the tip and from the pit cavity to and through the skin. Externally, this yellow segment appears as a narrow yellow stripe along the suture line. Occasionally, yellow areas accur in the flesh in locations other than along the suture.

Asexual reproduction shows that these characteristics hold true through succeeding propagations.

In the accompanying illustrations (reading from left to right) is shown a transverse section of a specimen of the new variety fruit clearly depicting the distinct yellow marking stripe; an elevation view of a specimen of the whole fruit; a second elevation of the suture side of a fruit specimen, showing the penetration of the marking stripe through the skin; and at the bottom a specimen of the foliage showing absence of the yellowish tint which is characteristic of yellow peach varieties.

The following is a detailed description of the new variety, giving color designations according to Ridgway's Color Standard and Horticultural Color Guide. Specimens described grown at Atlas, Illinois:

Dates of first and last picking: September 11th–September 15th.

Tree: Medium large; medium vigorous; open; spreading; vase formed; hardy; productive; regular bearer.

Trunk: Stocky; medium shaggy.

Branches: Stocky; smooth; glossy.

*Color.*—Cameo Brown, Plate XXVIII, Color No. 7, Tone K, overlaid with Pale Gull Gray, Plate LIII, Tone (10), Ridgway's Color Standard.

*Lenticels.*—Numerous; large.

Leaves: Length, 6''; width, 1⅝''. Medium large; oval; acutely pointed; medium thin; smooth.

*Color.*—Spinach Green, Plate o960, page 187, volume II, Horticultural Color Guide.

*Margin.*—Glandular; finely serrate.

*Petiole.*—Short; medium thick.

*Glands.*—Average number, 3. Large; alternate; reniform; free.

Flowers: Dates first and full blossoms—late compared with other varieties; medium small.

*Color.*—Azalea Pink, Color No. 618/2, page 74, volume I, Horticultural Color Chart.

Fruit: Eating—September 13th.

*Size.*—Uniform; large. *Axial diameter,* 3''; transverse in suture plane, 2⅞''; at right angles to suture plane, 2$\frac{13}{16}$''.

*Form.*—Uniform; symmetrical; globose.

*Suture.*—Distinct; shallow; extends from base but discontinues at apex; a thin yellow line marks line of suture.

*Ventral surface.*—Slightly lipped towards base. Apex—right side.

*Cavity.*—Abrupt; elongated in suture plane with suture showing on both sides. Depth, ½''; breadth, 1'' x 1⅛''. Markings—none.

*Base.*—Rounded.

*Apex.*—Rounded. Pistil point—apical.

*Stem.*—Length, $\frac{3}{16}$''; stout; glabrous. Adherence to stone—medium strong.

*Skin.*—Thin; tough; tenacious to flesh; tendency to break, none in wet or dry season. *Color*—Delft Rose, Plate o21/1, page 108, volume II, Horticultural Color Guide, shading to Rose Opal, Plate o22/1, page 110, volume II, Horticultural Color Guide. Down—scant; short. A narrow yellow (Buttercup Yellow, Color No. 5/1, page 5, Horticultural Color Guide) stripe extends along the suture line from the stem to the tip on one side of the fruit. This stripe is in distinct contrast to the typical "white peach" color (cream with red blush) of the rest of the skin.

Flesh:

*Color.*—White. Surface of pit cavity—color—Carmine, Plate 21/1, page 21, volume I, Horticultural Color Guide. A thin segment of yellow (Buttercup Yellow) Plate 5/1, page 5, Horticultural Color Chart, flesh extends from the base to the apex at the suture. This yellow segment is from $\frac{1}{32}''$ to $\frac{1}{16}''$ thick. It extends from the pit cavity to, and through, the skin, being visible externally along the suture. Occasionally yellow areas appear in the flesh at points other than the suture, showing as yellow marbled parts of the flesh which is otherwise white.

*Amygdalin.*—Scant. Juice—moderate; rich.

*Texture.*—Meaty.

*Fibres.*—Few; fine; tender.

*Ripens.*—Fairly even.

*Flavor.*—Subacid.

*Aroma.*—Distinct.

*Eating quality.*—Best.

Stone: Free.

*Fibres.*—Parts from flesh smoothly.

*Size.*—Small; length $1\frac{9}{16}''$; thickness $\frac{13}{16}''$.

*Form.*—Obovoid; full; cuneate toward base.

*Base.*—Oblique. Hilum—narrow; oval.

*Apex.*—Acute.

*Sides.*—Equal; curved on right and left sides. Surface—irregularly furrowed throughout; pitted throughout.

*Ridges.*—Rounded.

*Pits.*—Elongated. Ventral edge—thick with wing throughout.

*Dorsal edge.*—Narrow with deep narrow groove throughout. Ridges on either side—interrupted.

Use: Market; dessert; canning.

Keeping quality: Good.

Resistance to:

*Insects.*—Medium good.

*Diseases.*—Medium.

Shipping quality: Good.

I claim:

A new and distinct variety of peach tree characterized as to novelty by the white flesh of its fruit, marked with a thin yellow flesh segment extending along the suture line from stem to tip and through the skin, appearing externally as a narrow yellow stripe along said line; by the excellent flavor and quality of its fruit, slightly less acid than possessed by its parent variety; by the firmness of its flesh; and by the absence of the yellowish tint from the foliage, substantially as shown and described.

CHARLES O. GRISSINGER.

No references cited.